United States Patent
Inoue et al.

(10) Patent No.: US 10,695,215 B2
(45) Date of Patent: Jun. 30, 2020

(54) MULTILAYER FILM FOR DISPOSABLE BODY WARMER OUTER BAG, AND DISPOSABLE BODY WARMER

(71) Applicant: KOBAYASHI PHARMACEUTICAL CO., LTD., Osaka-shi, Osaka (JP)

(72) Inventors: Hiroyuki Inoue, Tokyo (JP); Takayuki Miyazaki, Tokyo (JP); Tsuyoshi Igaue, Osaka (JP); Yorikazu Kotani, Osaka (JP)

(73) Assignee: KOBAYASHI PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 15/738,833

(22) PCT Filed: Jun. 23, 2016

(86) PCT No.: PCT/JP2016/068594
§ 371 (c)(1),
(2) Date: Dec. 21, 2017

(87) PCT Pub. No.: WO2016/208650
PCT Pub. Date: Dec. 29, 2016

(65) Prior Publication Data
US 2018/0168856 A1    Jun. 21, 2018

(30) Foreign Application Priority Data
Jun. 23, 2015 (JP) .................. 2015-125934

(51) Int. Cl.
*A61F 7/03* (2006.01)
*B32B 27/32* (2006.01)
(Continued)

(52) U.S. Cl.
CPC .............. *A61F 7/034* (2013.01); *B32B 27/00* (2013.01); *B32B 27/30* (2013.01); *B32B 27/32* (2013.01);
(Continued)

(58) Field of Classification Search
CPC ... A61F 7/034; A61F 2007/038; B65D 65/40; B65D 81/24; B65D 65/22; F24V 30/00;
(Continued)

(56) References Cited

U.S. PATENT DOCUMENTS 3,784,434 A    1/1974  Paisley et al.
3,956,544 A *  5/1976  Harrington ............. B32B 27/00
                                                428/34.8
(Continued)

FOREIGN PATENT DOCUMENTS

EP    2 216 173 A1   8/2010
GB    2 125 730 A    3/1984
(Continued)

OTHER PUBLICATIONS

International Search Report, issued in PCT/JP2016/068594, dated Aug. 23, 2016.
(Continued)

*Primary Examiner* — Michael C Miggins
(74) *Attorney, Agent, or Firm* — Birch, Stewart, Kolasch & Birch, LLP (57) ABSTRACT

Provided is a multilayer film for a disposable body warmer outer bag, and a disposable body warmer, which are excellent in gas barrier property that inhibits permeation of oxygen gas, water vapor and the like, which can allow swelling due to hydrogen gas generated during a storage period to be prevented, and which are excellent in seal strength, impact resistance and weather resistance.
A disposable body warmer outer bag formed from a multilayer film comprising a first barrier layer (10) and a second
(Continued)

barrier layer (20), wherein the first barrier layer (10) and the second barrier layer (20) consist of a polyvinylidene chloride layer (12) or a polyvinylidene chloride layer (22) obtained by coating at least one surface (upper portion in FIG. 1) of a heat-resistant resin substrate (11) or a heat-resistant resin substrate (21) with polyvinylidene chloride.

7 Claims, 3 Drawing Sheets

(51) Int. Cl.
| | |
|---|---|
| *B32B 27/34* | (2006.01) |
| *B65D 65/40* | (2006.01) |
| *B65D 81/24* | (2006.01) |
| *B32B 27/30* | (2006.01) |
| *B32B 27/00* | (2006.01) |
| *B32B 27/36* | (2006.01) |
| *F24V 30/00* | (2018.01) |
| *B65D 65/22* | (2006.01) |
| *A61F 7/02* | (2006.01) |

(52) U.S. Cl.
CPC .............. *B32B 27/34* (2013.01); *B32B 27/36* (2013.01); *B65D 65/22* (2013.01); *B65D 65/40* (2013.01); *B65D 81/24* (2013.01); *F24V 30/00* (2018.05); *A61F 2007/022* (2013.01); *A61F 2007/0222* (2013.01); *A61F 2007/0244* (2013.01); *A61F 2007/0258* (2013.01); *A61F 2007/038* (2013.01); *B32B 27/302* (2013.01); *B32B 27/306* (2013.01); *B32B 27/308* (2013.01); *B32B 27/365* (2013.01)

(58) Field of Classification Search
CPC ......... B32B 27/00; B32B 27/30; B32B 27/32; B32B 27/34; B32B 27/36; B32B 27/302; B32B 27/306; B32B 27/308; B32B 27/365
See application file for complete search history.

(56) References Cited

U.S. PATENT DOCUMENTS

| | | | |
|---|---|---|---|
| 4,909,881 A * | 3/1990 | Garland | ................ B32B 27/08 |
| | | | 156/229 |
| 9,150,005 B2 | 10/2015 | Hsu et al. | |
| 2013/0156994 A1 | 6/2013 | Hsu et al. | |
| 2015/0240133 A1 | 8/2015 | Nakayama et al. | |

FOREIGN PATENT DOCUMENTS

| | | | |
|---|---|---|---|
| JP | 11-239584 A | 9/1999 |
| JP | 2002-120860 A | 4/2002 |
| JP | 2003-231221 A | 8/2003 |
| JP | 2008-143103 A | 6/2008 |
| JP | 2011-230451 A | 11/2011 |
| TW | 201323170 A1 | 6/2013 |
| TW | 201431992 A | 8/2014 |

OTHER PUBLICATIONS

Written Opinion of the International Searching Authority, issued in PCT/JP2016/068594, dated Aug. 23, 2016.
Database WPI, Week 197429, Thomson Scientific, London, GB; AN 1974-52977V, XP-002785607 & JP 49-24587 B2, Jun. 24, 1974, abstract.
Database WPI, Week 199111, Thomson Scientific, London, GB; AN 1991-078427, XP-002785608 & JP 3-26528 A, Feb. 5, 1991, abstract.
Database WPI, Week 200419, Thomson Scientific, London, GB; AN 2004-194350, XP-002785613 & JP 2003-231221 A, Aug. 19, 2003, abstract.
European Patent Office Communication and extended search report issued in the corresponding European Patent Application No. 16814419.4 dated Oct. 19, 2018.
U.S. Appl. No. 15/329,930, filed Jan. 27, 2017.

* cited by examiner

MULTILAYER FILM FOR DISPOSABLE BODY WARMER OUTER BAG, AND DISPOSABLE BODY WARMER

TECHNICAL FIELD

The present invention relates to a multilayer film for a disposable body warmer outer bag, and a disposable body warmer.

BACKGROUND ART

A disposable body warmer is a body warmer utilizing heat generation due to the oxidation action of iron powder, and is usually formed by accommodating, and packaging airtightly an inner bag that accommodates, in an air-permeable bag of a non-woven fabric, paper or the like, an exothermic composition containing iron powder as an exothermic element, a salt as an oxidation catalyst, activated carbon for intake of oxygen, water for oxidizing iron, a water-retaining agent for retaining water, and the like, in an outer bag made of an air-impermeable film for cutting off contact with air in an unused state.

A disposable body wanner outer bag is required to be excellent in gas barrier property that inhibits permeation of air, especially, oxygen gas, water vapor, and the like. If the disposable body warmer outer bag is poor in gas barrier property against oxygen gas and water vapor, any gas and water vapor in the disposable body wanner outer bag escape outside during storage for a long period to thereby produce a depressurized (vacuum) state, and therefore the outer bag is depressed and thus is not preferable in terms of appearance. In addition, when such a disposable body warmer outer bag in a depressurized (vacuum) state is stored for a long period and thereafter used for a disposable body wanner, the duration of heat generation is often short. As the air-impermeable film forming the disposable body warmer outer bag, a multilayer film is generally used where a gas barrier layer is provided on a sealant layer and a heat-resistant resin layer is provided on an outermost layer. Two of such air-impermeable multilayer films are superposed and the peripheries of the sealant layers located inward are mutually heat-sealed to form a bag, thereby producing the disposable body warmer outer bag.

As the air-impermeable film forming such a disposable body warmer outer bag, for example, an air-impermeable multilayer film has been used where a coating film of polyvinylidene chloride is provided on one surface of a substrate film such as a polyolefin-based resin film and a heat-sealing resin layer of an ethylene-vinyl acetate copolymer or the like is further provided thereon. The air-impermeable multilayer film, however, has the problem of deterioration in heat generation-maintaining property due to storage for a long period. In order to solve the problem, an air-impermeable multilayer film is proposed where a polyethylene terephthalate film covered with an aluminum oxide layer, a polyethylene film as an adhesion layer, and an ethylene-vinyl acetate copolymer as a heat-sealing resin layer are provided (PTL 1).

Meanwhile, it is known that, when a disposable body warmer is stored in an unused state for a long period, a trace amount of hydrogen gas is generated. A disposable body warmer outer bag is swollen by hydrogen gas, and is not preferable in terms of appearance. In addition, if marginally swollen, the outer bag is broken, and an exothermic composition accommodated in an inner bag is oxidized to generate heat, thereby causing the function as a disposable body warmer to be impaired. Therefore, the disposable body warmer outer bag is required to have a hydrogen permeation property so that the outer bag is not swollen during storage for a long period. The disposable body warmer outer bag, however, is also required to be excellent in gas barrier property that inhibits permeation of oxygen gas, water vapor and the like, as described above. Therefore, if the gas barrier property of the air-impermeable film forming the disposable body warmer outer bag is enhanced, a hydrogen gas permeation property is deteriorated to result in swelling during storage for a long period. The Applicant has then proposed, as one that satisfies both conflicting conditions of a gas barrier property against oxygen gas and water vapor and a hydrogen gas permeation property, a multilayer film including a vapor-deposited layer obtained by vapor-depositing a metal or metal oxide on a substrate, and a polyvinylidene chloride layer obtained by coating the substrate with polyvinylidene chloride, and a disposable body warmer where the multilayer film is used for an outer bag has been marketed by the Applicant.

The multilayer film including the vapor-deposited layer and the polyvinylidene chloride layer not only is excellent in gas barrier property that inhibits permeation of oxygen gas, water vapor and the like, but also can allow swelling due to hydrogen gas generated during storage to be prevented. Thus, the multilayer film including the vapor-deposited layer and the polyvinylidene chloride layer has no large problem when used as an outer bag for a disposable body warmer, but the Applicant has made studies and as a result has found the following points to be improved.

(1) Durability during Distribution as Product

An outer bag may be subjected to external high impact, and therefore an outer bag made of an air-impermeable film is demanded to have seal strength between respective layers and impact resistance so that the outer bag is neither opened nor ruptured even when subjected to impact.

(2) Weather Resistance during Display at Store Front

An outer bag may be exposed to ultraviolet light such as sunlight, and therefore an outer bag made of an air-impermeable film is demanded to have weather resistance so that the change in appearance such as discoloration is not caused even after exposure to ultraviolet light such as sunlight.

While the multilayer film including the vapor-deposited layer and the polyvinylidene chloride layer not only is excellent in gas barrier property, but also can allow swelling due to hydrogen gas to be prevented, as described above, it has been found to have room for improvement in seal strength, impact resistance and weather resistance.

As described above, various multilayer films for disposable body warmer outer bag are proposed, but a multilayer film for a disposable body warmer outer bag, and a disposable body warmer are required which can ensure an optimum gas permeation property and gas barrier property as a product over a long period and which are excellent in seal strength, impact resistance and weather resistance.

CITATION LIST

Patent Literatures

PTL 1:. Japanese Patent Laid-Open No. 11-239584

SUMMARY OF INVENTION

Technical Problem

An object of the present invention is then to provide a multilayer film for a disposable body warmer outer bag, and a disposable body warmer that are excellent in gas barrier property which selectively inhibits permeation of oxygen gas, water vapor and the like, that can allow swelling due to hydrogen gas generated during storage to be prevented, and that are excellent in seal strength, impact resistance and weather resistance, in particular, that can withstand storage (display) for a long period in the state of being exposed to ultraviolet light such as sunlight.

Solution to Problem

The present inventors have made intensive studies in order to solve the above problem, and as a result, have found that a multilayer film including two or more barrier layers consisting of a substrate and a polyvinylidene chloride layer obtained by coating at least one surface of the substrate with polyvinylidene chloride can realize optimal oxygen gas permeation property, water vapor permeation property, hydrogen gas permeation property, seal strength, impact resistance and weather resistance as a disposable body warmer outer bag, thereby leading to completion of the present invention. Specific aspects of the present invention are as follows.

[1] A multilayer film for a disposable body warmer outer bag, comprising two or more barrier layers consisting of a substrate and a polyvinylidene chloride layer obtained by coating at least one surface of the substrate with polyvinylidene chloride.

[2] The multilayer film for a disposable body warmer outer bag according to [1], not comprising any vapor-deposited layer obtained by vapor-depositing a metal or metal oxide.

[3] The multilayer film for a disposable body warmer outer bag according to [1] or [2], wherein the substrate is selected from biaxially oriented polypropylene, biaxially oriented polyethylene terephthalate and a biaxially oriented polyamide resin.

[4] The multilayer film for a disposable body warmer outer bag according to any one of [1] to [3], further comprising a sealant layer comprising a thermal fusible resin substrate.

[5] The multilayer film for a disposable body warmer outer bag according to any one of [1] to [4], further comprising an adhesive layer between the two or more barrier layers.

[6] The multilayer film for a disposable body warmer outer bag according to any one of [1] to [5], further comprising an additional resin layer.

[7] The multilayer film for a disposable body warmer outer bag according to any one of [1] to [6], wherein an oxygen permeability measured at 20° C. and 90% RH is 1.5 to 4.5 cc/(m²·day·atm), and a water vapor permeability measured at 40° C. and 90% RH is 0.05 to 3.5 g/(m²·day).

[8] A disposable body warmer obtained by packaging airtightly an inner bag accommodating an exothermic composition, in an outer bag formed by thermal fusion of the multilayer film for a disposable body warmer outer bag according to any one of [1] to [7].

Advantageous Effects of Invention

The multilayer film for a disposable body warmer outer bag of the present invention has an optimal gas barrier property for a disposable body warmer outer bag that inhibits permeation of oxygen gas and water vapor and that also permits permeation of hydrogen, gas, and the multilayer film is excellent in seal strength, impact resistance and weather resistance.

The disposable body warmer of the present invention can allow swelling due to hydrogen gas generated during storage and degradation of an exothermic composition due to permeation of oxygen gas and water vapor to be prevented, and can be stored for a long period with no function as a disposable body warmer being impaired. In addition, the disposable body warmer of the present invention is excellent in seal strength, impact resistance and weather resistance, therefore is excellent in durability during distribution, and also hardly causes the change in appearance such as discoloration even when exposed to ultraviolet light such as sunlight during display at a store front.

DESCRIPTION OF EMBODIMENTS

Hereinafter, the multilayer film for a disposable body warmer outer bag and the disposable body warmer of the present invention are described with reference to the drawings.

The multilayer film for a disposable body warmer outer bag of the present invention includes two or more barrier layers consisting of a substrate and a polyvinylidene chloride layer obtained by coating at least one surface of the substrate with polyvinylidene chloride. The substrates of the respective barrier layers in the two or more barrier layers may be the same as or different from each other.

The number of the barrier layers is not particularly limited as long as it is two or more. Such layers are desirably thin and desirably exhibit impact resistance and weather resistance, and the number thereof is preferably 2 to 5, more preferably 2 to 3, most preferably 2.

Figure 1:
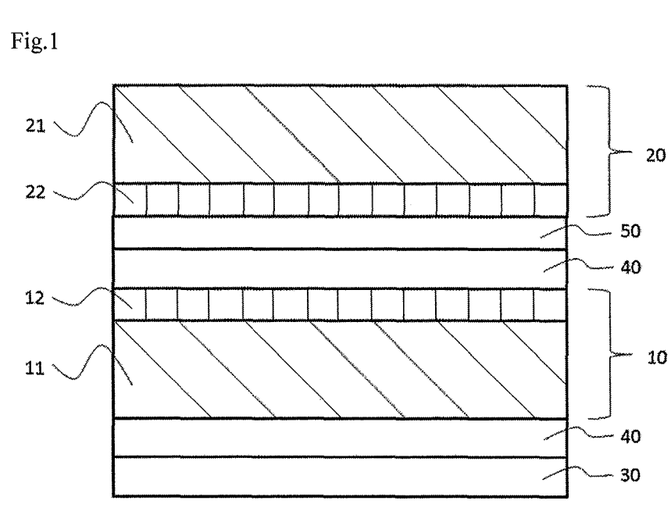
FIG. 1 is an explanatory view illustrating a lamination configuration according to one embodiment of the multilayer film for a disposable body warmer outer bag of the present invention.
Figure 2:
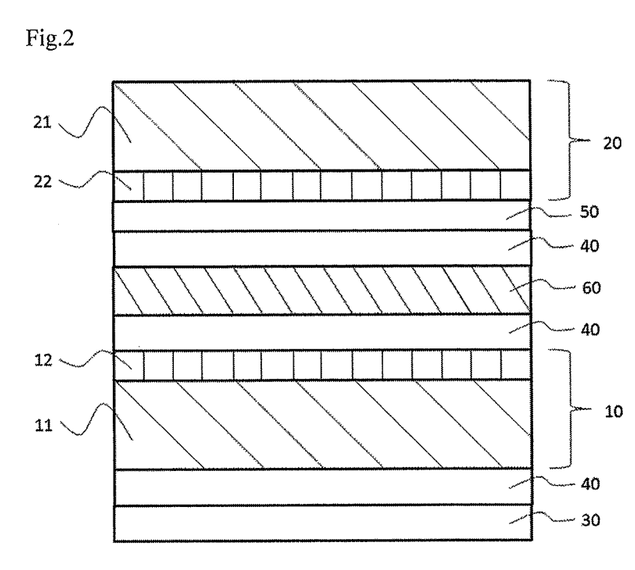
FIG. 2 is an explanatory view illustrating a lamination configuration according to another embodiment of the multilayer film for a disposable body warmer outer bag of the present invention.
Figure 3:
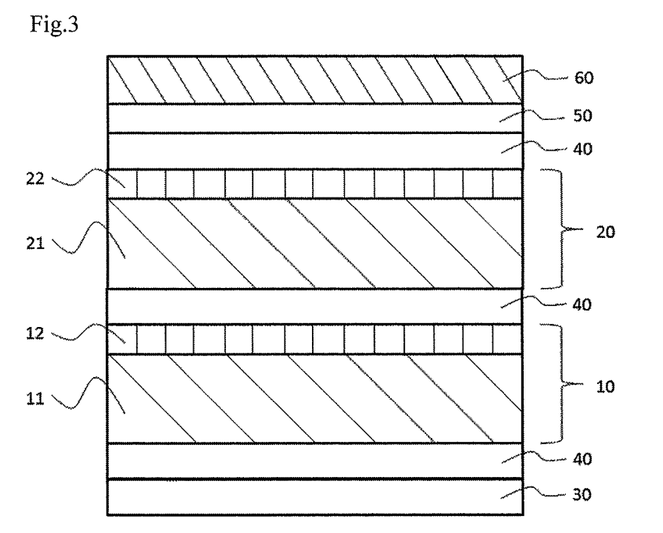
FIG. 3 is an explanatory view illustrating a lamination configuration according to still another embodiment of the multilayer film for a disposable body warmer outer bag of the present invention.

FIGS. 1 to 3 illustrate embodiments of the multilayer film for a disposable body warmer outer bag of the present invention. The multilayer film for a disposable body warmer outer bag includes a first barrier layer 10, a second barrier layer 20 and a sealant layer 30. In a disposable body warmer outer bag, the sealant layer 30 serves as an inner surface of the outer bag.

In FIG. 1, the first barrier layer 10 consists of a polyvinylidene chloride layer 12 obtained by coating at least one surface (upper portion in FIG. 1) of a heat-resistant resin substrate 11 with polyvinylidene chloride. The second barrier layer 20 consists of a polyvinylidene chloride layer 22 obtained by coating at least one surface (lower portion in FIG. 1) of a heat-resistant resin substrate 21 with polyvinylidene chloride. In the embodiment illustrated in FIG. 1, an adhesive layer 40 and a sealant layer 30 are laminated under the first barrier layer 10, and an adhesive layer 40 and a printing ink layer 50 are laminated on the first barrier layer 10. The adhesive layers 40 are used for adhesion of the first barrier layer 10 to the sealant layer 30, the second barrier layer 20 or another layer (for example, the printing ink layer 50 in FIG. 1). The printing ink layer 50 can be, if necessary, provided for printing of product description and the like.

In the embodiment illustrated in FIG. 2, the configuration in FIG. 1 further includes an additional adhesive layer 40 and an additional resin layer 60 between the first barrier layer 10 and the second barrier layer 20. The additional resin layer 60 provided therebetween enhances strength of the multilayer film. In addition, the additional resin layer 60 can be provided to thereby increase the entire thickness of the multilayer film, thereby resulting in further decreases in gas permeation property and water vapor permeation property.

In the embodiment illustrated in FIG. 3, an adhesive layer 40 is laminated on the sealant layer 30, the first barrier layer 10 is then laminated thereon so that the heat-resistant resin substrate 11 and the polyvinylidene chloride layer 12 are located in this order, an adhesive layer 40 is further laminated thereon and the second barrier layer 20 is additionally laminated thereon so that the heat-resistant resin substrate 21 and the polyvinylidene chloride layer 22 are located in this order, and an adhesive layer 40 and the printing ink layer 50 are further interposed in this order and the additional resin layer 60 is laminated thereon so as to serve as an outermost layer.

A disposable body warmer outer bag configured from the multilayer film for a disposable body warmer outer bag of the present invention illustrated in each of FIGS. 1 to 3 includes the polyvinylidene chloride layer 12 obtained by coating at least one surface of the heat-resistant resin substrate 11 with polyvinylidene chloride, as the first barrier layer 10, and the polyvinylidene chloride layer 22 obtained by coating at least one surface of the heat-resistant resin substrate 21 with polyvinylidene chloride, as the second barrier layer 20, thereby blocking penetration of oxygen from the exterior of the outer bag into the interior of the outer bag at a certain level and permitting permeation of hydrogen from the interior of the outer bag into the exterior of the outer bag. Thus, a metal such as iron powder in an exothermic composition accommodated in a disposable body warmer inner bag is effectively prevented from being oxidized before use, and also the outer bag is effectively prevented from being swollen due to hydrogen generated during storage. Furthermore, the first barrier layer 10 and the second barrier layer 20 are provided to thereby enhance a water vapor barrier property that prevents permeation of water vapor. Thus, moisture is prevented from penetrating from the exterior of the outer bag into the interior of the outer bag, and water serving to promote oxidation of a metal such as iron powder included, as a constituent, in the exothermic composition of the disposable body warmer is also prevented from being discharged as water vapor from the interior of the outer bag toward the exterior of the outer bag. Additionally, the first barrier layer 10 and the second barrier layer 20 are provided to thereby impart excellent seal strength and impact resistance. Thus, the outer bag can be prevented from being opened and ruptured even when subjected to high impact. In addition, the first barrier layer 10 and the second barrier layer 20 are provided to thereby impart excellent weather resistance. Thus, even when the outer bag is exposed to ultraviolet light such as sunlight, the change in appearance, such as discoloration, is prevented.

Next, constituents and a production method of the multilayer film for a disposable body warmer outer bag of the present invention are described.

The first barrier layer 10 consists of the polyvinylidene chloride layer 12 obtained by coating the heat-resistant resin substrate 11 with polyvinylidene chloride. In addition, the second barrier layer 20 consists of the polyvinylidene chloride layer 22 obtained by coating the heat-resistant resin substrate 21 with polyvinylidene chloride.

For the heat-resistant resin substrate 11 and the heat-resistant resin substrate 21, for example, any film of various resins such as a polyolefin-based resin such as a polyethylene-based resin or a polypropylene-based resin, a cyclic polyolefin-based resin, a polystyrene-based resin, an acrylonitrile-styrene copolymer (AS resin), an acrylonitrile-butadiene-styrene copolymer (ABS resin), a poly(meth)acrylic-based resin, a polycarbonate-based resin, a polyester-based resin such as polyethylene terephthalate and polyethylene naphthalate, a polyamide-based resin such as various nylons, a polyurethane-based resin, an acetal-based resin, and a cellulose-based resin can be used. Among them, a film of a polyester-based resin, a polyolefin-based resin or a polyamide-based resin is preferable, and in particular, a film of biaxially oriented polypropylene, biaxially oriented polyethylene terephthalate or a biaxially oriented polyamide resin is preferable. Various resin films can be formed by a method where one or more of the above various resins are used and such resins are subjected singly or in combinations of two or more to multilayer co-extrusion film formation with an extrusion method, a cast molding method, a T-die method, a cutting method, an inflation method, or other film formation methods, furthermore by a method where two or more of the resins are mixed, and subjected to film formation, or the like; and can be further uniaxially or biaxially oriented by utilizing, for example, a tentering system or a tubular system.

The thicknesses of the heat-resistant resin substrate 11 and the heat-resistant resin substrate 21 are preferably 3 to 500 μm, more preferably 5 to 300 μm, further preferably 10 to 100 μm, most preferably 15 to 50 μm.

Various resin films for use in the heat-resistant resin substrate 11 and the heat-resistant resin substrate 21 may be the same as or different from each other in terms of the type and/or the thicknesses thereof.

The polyvinylidene chloride resin with which the heat-resistant resin substrate 11 and the heat-resistant resin substrate 21 is coated is preferably a homopolymer or copolymer of vinylidene chloride. As such a polymer, a vinylidene chloride copolymer where the content of vinylidene chloride is preferably in a range from 50 to 98% by mol, more preferably in a range from 75 to 96% by mol, is preferable because of being excellent in a balance between a film formation property and gas barrier property. As the monomer copolymerizable with vinylidene chloride, for example, vinyl chloride, acrylic acid esters such as methyl acrylate, ethyl acrylate, butyl acrylate, 2-ethylhexyl acrylate and 2-hydroxyethyl acrylate, methacrylic acid esters such as methyl methacrylate and glycidyl methacrylate, acrylonitrile, methacrylonitrile, and unsaturated carboxylic acids such as acrylic acid, methacrylic acid, itaconic acid and maleic acid can be selected and used singly or in combinations of two or more. Among them, vinyl chloride or acrylic acid ester is preferably used in terms of a film formation property. In addition, the polyvinylidene chloride resin can also be used in appropriate combinations of two or more. Furthermore, the polyvinylidene chloride resin, to which any additive such as a heat stabilizer, a light stabilizer, and a lubricant is appropriately added, can also be used. The polyvinylidene chloride resin is usually used as an emulsion or a solution.

Such a polyvinylidene chloride layer 12 and a polyvinylidene chloride layer 22 can be formed by, for example, a method where the polyvinylidene chloride resin which is, if necessary, dissolved or dispersed in a solvent and thus formed into an application liquid is applied onto the surface of the heat-resistant resin substrate 11 and the heat-resistant resin substrate 21.

The thicknesses of the polyvinylidene chloride layer 12 and the polyvinylidene chloride layer 22 are not particularly limited, may be appropriately set depending on the desired oxygen gas barrier property and the like, and is preferably 0.5 to 30 μm, more preferably 0.8 to 10 μm, most preferably 1 to 2 μm.

The polyvinylidene chloride layer 12 and the polyvinylidene chloride layer 22 may be the same as or different from each other in terms of the forming methods and/or the thicknesses thereof.

In the multilayer film for a disposable body warmer outer bag, the location of the polyvinylidene chloride layer 12 when viewed from the heat-resistant resin substrate 11, and the location of the polyvinylidene chloride layer 22 when viewed from the heat-resistant resin substrate 21 are not particularly limited, and may be any of the location closer to the sealant layer 30 (an inner surface of the outer bag) or the location opposite to the sealant layer 30 (an inner surface of the outer bag) when viewed from the heat-resistant resin substrate 11 or the heat-resistant resin substrate 21. When the second barrier layer 20 serves as an outer surface of the outer bag as in FIGS. 1 and 2, the location of the polyvinylidene chloride layer 22 is preferably closer to the sealant layer 30 (inner surface of the outer bag) when viewed from the heat-resistant resin substrate 21, from the viewpoint that deterioration in gas barrier property due to damage of the polyvinylidene chloride layer by the contact thereof with the exterior is prevented.

The oxygen permeability (20° C., 90% RH) of the first barrier layer by itself and/or the second barrier layer by itself are/is preferably 1.5 to 20 cc/($m^2$·day·atm), more preferably 2.0 to 15 cc/($m^2$·day·atm), most preferably 2.0 to 10 cc/($m^2$·day·atm). In addition, the water vapor permeability (40° C. and 90% RH) of the first barrier layer by itself and/or the second barrier layer by itself are/is preferably 1.0 to 20 g/($m^2$·day), more preferably 2.5 to 15 g/($m^2$·day).

The oxygen permeability (20° C. and 90% RH) of the multilayer film for a disposable body warmer outer bag, including the first barrier layer 10 and the second barrier layer 20, of the present invention is preferably 1.5 to 4.5 cc/($m^2$·day·atm), more preferably 2.0 to 4.0 cc/($m^2$·day·atm), most preferably 2.0 to 3.5 cc/($m^2$·day·atm), and the water vapor permeability (40° C. and 90% RH) thereof is preferably 0.05 to 3.5 g/($m^2$·day), more preferably 0.05 to 3.0 g/($m^2$·day), most preferably 0.05 to 2.5 g/($m^2$·day). The multilayer film for a disposable body warmer outer bag, including the first barrier layer 10 and the second barrier layer 20, of the present invention can have such oxygen permeability and water vapor permeability in the above numerical ranges, to thereby exert the following effects: a gas barrier property that inhibits permeation of oxygen gas, water vapor and the like is excellent and swelling due to hydrogen gas generated during storage can be prevented.

The sealant layer 30 preferably consists of a thermal fusible resin. As the thermal fusible resin, low density polyethylene, medium density polyethylene, high density polyethylene, straight-chain (linear) low density polyethylene, polypropylene, an ethylene-vinyl acetate copolymer, an ionomer resin, an ethylene-ethyl acrylate copolymer, an ethylene-acrylic acid copolymer, an ethylene-methacrylic acid copolymer, an ethylene-propylene copolymer, a methylpentene polymer, and an acid-modified polyolefin-based resin where a polyolefin-based resin such as polyethylene, polystyrene or polypropylene is modified with an unsaturated carboxylic acid such as acrylic acid, methacrylic acid, maleic anhydride or fumaric acid, as well as other resins can be used singly or in combinations of two or more. Various resin films can be formed by a method where one or more of the above various resins are used and such resins are subjected singly or in combinations of two or more to multilayer co-extrusion film formation with an extrusion method, a cast molding method, a T-die method, a cutting method, an inflation method, or other film formation methods, or furthermore by a method where two or more of the resins are mixed prior to film formation and the resultant is further uniaxially or biaxially oriented by utilizing, for example, a tentering system or a tubular system. Among them, unoriented polypropylene, biaxially oriented polypropylene, unoriented polyethylene, low density polyethylene, medium density polyethylene, high density polyethylene or straight-chain (linear) low density polyethylene is preferable, and in particular, unoriented polypropylene, biaxially oriented polypropylene or straight-chain (linear) low density polyethylene is more preferable in terms of thermal fusion property.

In addition, the thickness of the sealant layer 30 is preferably 5 to 300 μm, more preferably 10 to 100 μm, most preferably 15 to 50 μm.

The location of the sealant layer 30 in the multilayer film for a disposable body warmer outer bag is not particularly limited and may be provided on an inner surface of the outer bag, and may also be provided on an outer surface of the outer bag.

The multilayer film for a disposable body warmer outer bag of the present invention may be provided with the adhesive layer 40 as a constituent at any location, and preferably, the adhesive layer 40 is provided between the first barrier layer 10 and the second barrier layer 20 and the first barrier layer 10 and second barrier layer 20 are laminated with being bonded to each other. As the adhesive forming the adhesive layer, any adhesive usually used in the multilayer film for a disposable body warmer outer bag can be used without any limitation, and for example, an ether-based adhesive, a polyvinyl acetate-based adhesive, a polyacrylic acid ester-based adhesive made of a homopolymer of acrylic acid ethyl, butyl or 2-ethylhexyl ester, or a copolymer thereof with methyl methacrylate, acrylonitrile, styrene or the like, a cyanoacrylate-based adhesive, an ethylene copolymer-based adhesive made of a copolymer of ethylene with a monomer such as vinyl acetate, ethyl acrylate, acrylic acid or methacrylic acid, a cellulose-based adhesive, a polyester-based adhesive, a polyamide-based adhesive, a polyimide-based adhesive, an amino resin-based adhesive made of a urea resin, a melamine resin or the like, a phenol resin-based adhesive, an epoxy-based adhesive, a polyurethane-based adhesive, a reaction (meth)acrylic-based adhesive, a rubber-based adhesive made of a chloroprene rubber, a nitrile rubber, a styrene-butadiene rubber or the like, a silicone-based adhesive, an inorganic adhesive made of alkali metal silicate, low melting point glass or the like, or other adhesives can be used. The composition faun of the adhesive may be any composition form such as an aqueous form, a solution form, an emulsion form and a dispersion form. In addition, the form of the adhesive may be any form such as a film-sheet form, a powder form and a solid form. Furthermore, the adhesion mechanism may be any mechanism such as chemical reaction, solvent volatilization, thermal fusion and thermal pressure mechanisms. Any mode usually used can be used as a usage mode of the adhesive without any limitation, and the adhesive layer can be formed by, for example, applying the adhesive onto at least one of the first barrier layer 10 or the second barrier layer 20 by a roll coating method, a gravure roll coating method, a kiss coating method, other coating methods, a printing method or the like, and then drying a solvent and the like. The content of the adhesive is preferably 0.1 to 10 g/m² (dry state), more preferably 0.5 to 8 g/m² (dry state), most preferably 1.5 to 4 g/m² (dry state).

In the multilayer film for a disposable body warmer outer bag of the present invention, the printing ink layer 50 may be provided as a constituent at any location. The printing ink layer 50 can be formed by adding one or more usual ink vehicles as a main component, arbitrarily adding, if necessary, one or more additives such as a plasticizer, a stabilizer, an antioxidant, a light stabilizer, an ultraviolet absorber, a curing agent, a crosslinking agent, a lubricant, an antistatic agent and a filler thereto, further adding a colorant such as a dye/pigment thereto, and sufficiently kneading the resultant with a solvent, a diluent or the like to prepare an ink composition; and then printing a desired character, graphic, sign, pattern and the like with the ink composition by, for example, gravure printing, offset printing, relief printing, screen printing, transfer printing, flexographic printing or other printing systems.

Any ink vehicle usually used for the disposable body warmer outer bag can be used as the ink vehicle without any limitation, and examples can include flaxseed oil, tung oil, soybean oil, hydrocarbon oil, rosin, rosin ester, a rosin-modified resin, shellac, an alkyd resin, a phenol-based resin, a maleic acid resin, a natural resin, a hydrocarbon resin, a polyvinyl chloride-based resin, a polyvinyl acetate-based resin, a polystyrene-based resin, a polyvinyl butyral resin, an acrylic or methacrylic-based resin, a polyamide-based resin, a polyester-based resin, a polyurethane-based resin, an epoxy-based resin, a urea resin, a melamine resin, an amino alkyd-based resin, nitrocellulose, ethyl cellulose, a chlorinated rubber and a cyclized rubber singly or in combinations of two or more.

The content of the printing ink layer 50 is preferably 0.1 to 10 g/m² (dry state), more preferably 0.5 to 8 g/m² (dry state), most preferably 1 to 5 g/m² (dry state).

The multilayer film for a disposable body warmer outer bag of the present invention may further include an additional resin layer 60. The additional resin layer 60 may be a layer formed from any resin as long as gas permeation property and water vapor permeation property of the multilayer film for a disposable body warmer outer bag of the present invention are not impaired, and the additional resin layer 60 can be provided at any desired position depending on the characteristics of the resin. For example, when the thermal fusible resin which is described above to be able to be used as the sealant layer 30 is used in the additional resin layer 60, it can be provided outward against the sealant layer 30 and used as a heat-sealing portion in formation of an outer bag. In addition, when the heat-resistant resin which is described above to be able to be used as the substrate of each of the first barrier layer 10 and the second barrier layer 20 is used in the additional resin layer 60, the heat-resistant resin can be provided between the first barrier layer 10 and the second barrier layer 20 to enhance the strength of the multilayer film, or can be provided opposite to the sealant layer 30 and outward against the second barrier layer 20, namely at a location so as to correspond to the outer surface of the disposable body warmer outer bag, thereby functioning as a protection film.

The thickness of the additional resin layer 60 is not particularly limited, and is preferably 3 to 500 µm, more preferably 5 to 300 µm, further preferably 5 to 100 µm, most preferably 5 to 50 µm.

The multilayer film for a disposable body warmer outer bag of the present invention can preferably realize an oxygen permeability (20° C. and 90% RH) of 1.5 to 4.5 cc/(m²·day·atm), more preferably 2.0 to 4.0 cc/(m²·day·atm), most preferably 2.0 to 3.5 cc/(m²·day·atm), and preferably realize a water vapor permeability (40° C. and 90% RH) of 0.05 to 3.5 g/(m²·day), more preferably 0.05 to 3.0 g/(m²·day), most preferably 0.05 to 2.5 g/(m²·day). The multilayer film for a disposable body warmer outer bag of the present invention can have such oxygen permeability and water vapor permeability in the above numerical ranges, to thereby exert the following effects: a gas barrier property that inhibits permeation of oxygen gas, water vapor and the like is excellent and swelling due to hydrogen gas generated during storage can be prevented. In order to stably store a disposable body warmer for a long period, both the oxygen permeability and the water vapor permeability are required to be in the above ranges, and, if any one of the permeabilities is outside the range, no desired effects can be achieved.

The multilayer film for a disposable body warmer outer bag of the present invention can preferably realize a seal strength of 15.0 N/15 mm or more, more preferably 20.0 N/15 mm or more, most preferably 25.0 N/15 mm or more. The multilayer film for a disposable body warmer outer bag of the present invention can have such seal strength within the above numerical range, to thereby exert the following effect: the outer bag is hardly opened or ruptured even when subjected to external high impact.

The multilayer film for a disposable body warmer outer bag of the present invention preferably does not include any vapor-deposited layer obtained by vapor-depositing a metal or metal oxide. If the multilayer film for a disposable body warmer outer bag of the present invention includes a vapor-deposited layer obtained by vapor-depositing a metal or metal oxide, the vapor-deposited layer may be changed in quality, color, and the like, thereby causing the appearance of the multilayer film for a disposable body warmer outer bag to be deteriorated, or not exhibiting an inherent gas barrier property and the like. The reason why such a phenomenon occurs is not clear, but it is considered that gas such as hydrogen chloride which can be generated from the polyvinylidene chloride layer 12 and/or the polyvinylidene chloride layer 22 can have any adverse effect on the vapor-deposited layer.

Next, the method for producing each of the multilayer film for a disposable body warmer outer bag and the disposable body warmer outer bag of the present invention is described.

The multilayer film for a disposable body warmer outer bag of the present invention can be produced by pressure bonding of a heat-resistant resin coated with a polyvinylidene chloride resin, serving as the first barrier layer 10, a heat-resistant resin coated with a polyvinylidene chloride resin, serving as the second barrier layer 20, the sealant layer 30, and an adhesive serving as the adhesive layer 40, as well as, if necessary, the printing ink layer 50 and the additional resin layer 60 being laminated, by use of a roll or the like.

Next, two of the multilayer films for a disposable body warmer outer bag can be superposed so that surfaces of the sealant layer 30 face each other, and the peripheries of the sealant layer 30 can be heat-sealed to form a bag, thereby producing a disposable body warmer outer bag. Any mode usually used can be used as the mode of heat-sealing without any limitation, and any heat-sealing form such as lateral sealing, two-side sealing, three-side sealing, four-side sealing, envelope-seam sealing, butt-seam sealing (pillow sealing), pleat sealing, flat bottom sealing, square bottom sealing, and gusset sealing forms may be adopted. Any heat-sealing method usually used can be used as the heat-sealing method without any limitation, and for example, bar sealing, rotating roll sealing, belt sealing, impulse sealing, high-frequency sealing, and ultrasonic sealing may be adopted.

The disposable body warmer of the present invention is obtained by packaging airtightly an inner bag accommodating an exothermic composition, in a disposable body warmer outer bag fanned from the multilayer film for a disposable body warmer outer bag.

The exothermic composition may be an exothermic composition for use in a usual disposable body warmer, and is not particularly limited. For example, an exothermic composition may be adopted which contains metal powder such as iron powder, a reaction aid such as salt, activated carbon, a water-retaining agent, water and the like. Specifically, for example, an exothermic composition can be formed from 100 parts by weight of metal powder, for example, iron powder such as reduced iron powder or cast iron powder, or aluminum powder, 3 to 10 parts by weight of a reaction aid such as sodium chloride, 20 to 40 parts by weight of activated carbon and a water-retaining agent, 30 to 90 parts by weight of water, and the like. Herein, for example, an alkali metal hydroxide and a weakly basic alkali metal salt such as sodium hydroxide, potassium hydroxide, sodium hydrogen carbonate and sodium tertiary phosphate can be added as a hydrogen generation inhibitor to the exothermic composition, and the amount thereof to be used can be a trace amount relative to the metal powder.

In addition, the inner bag accommodating the exothermic composition may be air-permeable to such an extent that a metal can generate heat in the presence of oxygen, and for example, a bag article where one surface is prepared by an air-permeable packaging material and the other surface is prepared by an air-impermeable packaging material, or a bag article where both surfaces are each prepared by an air-permeable packaging material can be used. As the air-permeable packaging material, for example, a woven fabric or a non-woven fabric, a porous sheet where a plastic film, sheet or the like is perforated, or a composite sheet thereof can be used. In addition, as the air-impermeable packaging material, for example, a polyethylene-based resin, a polypropylene-based resin, an ethylene-propylene copolymer, an ethylene-vinyl acetate copolymer, an ionomer resin, an ethylene-ethyl acrylate copolymer, an ethylene-acrylic acid or methacrylic acid copolymer, a methylpentene polymer, a polybutene-based resin, a polyvinyl acetate-based resin, a poly(meth)acrylic-based resin, a polyacrylonitrile-based resin, a polystyrene-based resin, an acrylonitrile-styrene copolymer (AS-based resin), an acrylonitrile-butadiene-styrene copolymer (ABS-based resin), a polyester-based resin, a polyamide-based resin, a polycarbonate-based resin, a polyvinyl alcohol-based resin, a saponified product of an ethylene-vinyl acetate copolymer, a fluororesin, a diene-based resin, a polyacetal-based resin, a polyurethane-based resin, nitrocellulose, or other known resins or films can be used. Any commonly known method can be used as the method for producing the inner bag without any limitation, and for example, any of various heat-sealing methods described above with respect to production of the outer bag can be preferably used.

EXAMPLES

Hereinafter, the present invention is more specifically described with reference to Examples and Comparative Examples.

Example 1

Production of Multilayer Film for Disposable Body Warmer Outer Package Illustrated in FIG. 1

A multilayer film for a disposable body warmer outer package, including first and second barrier layers 10 and 20 consisting of heat-resistant resin substrates 11 and 21 (biaxially oriented polypropylene films 11 and 21) and polyvinylidene chloride layers 12 and 22 obtained by coating at least one surface of each of the heat-resistant resin substrates 11 and 21 with polyvinylidene chloride, as illustrated in FIG. 1, was produced as follows.

A character, a graphic, a sign, a picture and the like were printed on a surface of a biaxially oriented polypropylene film 21 (thickness of biaxially oriented polypropylene film 21: 30 µm, thickness of polyvinylidene chloride layer 22: 1 µm, oxygen permeability: 9.7 cc/(m$^2$·day·atm), water vapor permeability: 4.4 g/(m$^2$·day)) having a polyvinylidene chloride layer 22, serving as the second barrier layer 20, the surface facing the polyvinylidene chloride layer 22, by use of a usual gravure ink composition with a gravure printing system, thereby forming a printing ink layer 50. Next, an ether-based adhesive was applied onto the printing ink layer 50 formed above, and dried to form an adhesive layer 40. A biaxially oriented polypropylene film 11 (thickness of biaxially oriented polypropylene film 11.: 30 µm, thickness of polyvinylidene chloride layer 12: 1 µm, oxygen permeability: 9.7 cc/(m$^2$·day·atm), water vapor permeability: 4.4 g/(m$^2$·day)) having a polyvinylidene chloride layer 12, serving as the first barrier layer 10 was placed on the adhesive layer 40 so that the polyvinylidene chloride layer 12 and the adhesive layer 40 were in contact with each other, and subjected to lamination and integration. An ether-based adhesive was then applied onto the biaxially oriented polypropylene film 11, and dried to form an adhesive layer 40. An unoriented polypropylene film 30 (thickness: 25 µm, oxygen permeability: 2400 cc/(m$^2$·day·atm), water vapor permeability: 14.4 g/(m$^2$·day)) was placed on the adhesive layer 40, and subjected to lamination and integration, thereby producing a multilayer film for a disposable body warmer outer bag, including unoriented polypropylene film 30/adhesive layer 40/biaxially oriented polypropylene film 11/polyvinylidene chloride layer 12/adhesive layer 40/printing ink layer 50/polyvinylidene chloride layer 22/biaxially oriented polypropylene film 21, when viewed from the lower layer.

Example 2

Production of Multilayer Film for Disposable Body Warmer Outer Package Illustrated in FIG. 1

A multilayer film for a disposable body warmer outer bag, including unoriented polypropylene film 30/adhesive layer 40/biaxially oriented polyethylene terephthalate film 11/polyvinylidene chloride layer 12/adhesive layer 40/printing ink layer 50/polyvinylidene chloride layer 22/biaxially oriented polypropylene film 21, when viewed from the lower layer, was produced in the same manner as in Example 1 except that a biaxially oriented polyethylene terephthalate film 11 (thickness of biaxially oriented polyethylene terephthalate film 11: 12 μm, thickness of polyvinylidene chloride layer 12: 1 μm, oxygen permeability: 8.1 cc/(m²·day·atm), water vapor permeability: 10 g/(m²·day)) having a polyvinylidene chloride layer 12 was used as the first barrier layer 10, instead of the biaxially oriented polypropylene film 11 (thickness of biaxially oriented polypropylene film 11: 30 μm, thickness of polyvinylidene chloride layer 12: 1 μm, oxygen permeability: 9.7 cc/(m²·day·atm), water vapor permeability: 4.4 g/(m²·day)) having a polyvinylidene chloride layer 12.

Example 3

Production of Multilayer Film for Disposable Body Warmer Outer Package Illustrated in FIG. 1

A multilayer film for a disposable body warmer outer bag, including unoriented polypropylene film 30/adhesive layer 40/biaxially oriented polyamide film 11/polyvinylidene chloride layer 12/adhesive layer 40/printing ink layer 50/polyvinylidene chloride layer 22/biaxially oriented polypropylene film 21, when viewed from the lower layer, was produced in the same manner as in Example 1 except that a biaxially oriented polyamide film 11 (thickness of biaxially oriented polyamide film 11: 25 μm, thickness of polyvinylidene chloride layer 12: 1 μm, oxygen permeability: 6.7 cc/(m²·day·atm), water vapor permeability: 9.7 g/(m²·day)) having a polyvinylidene chloride layer 12 was used as the first barrier layer 10, instead of the biaxially oriented polypropylene film 11 (thickness of biaxially oriented polypropylene film 11: 30 thickness of polyvinylidene chloride layer 12: 1 μm, oxygen permeability: 9.7 cc/(m²·day·atm), water vapor permeability: 4.4 g/(m²·day)) having a polyvinylidene chloride layer 12.

Example 4

Production of Multilayer Film for Disposable Body Warmer Outer Package Illustrated in FIG. 1

A multilayer film for a disposable body warmer outer bag, including unoriented polypropylene film 30/adhesive layer 40/biaxially oriented polyethylene terephthalate film 11/polyvinylidene chloride layer 12/adhesive layer 40/printing ink layer 50/polyvinylidene chloride layer 22/biaxially oriented polyethylene terephthalate film 21, when viewed from the lower layer, was produced in the same manner as in Example 1 except that biaxially oriented polyethylene terephthalate films 11 and 21 (thicknesses of biaxially oriented polyethylene terephthalate films 11 and 21: 12 μm, thicknesses of polyvinylidene chloride layers 12 and 22: 1 oxygen permeability: 8.1 cc/(m²·day·atm), water vapor permeability: 10 g/(m²·day)) having polyvinylidene chloride layers 12 and 22 were used as the first and second barrier layers 10 and 20, instead of the biaxially oriented polypropylene films 11 and 21 (thicknesses of biaxially oriented polypropylene films 11 and 21: 30 μm, thicknesses of polyvinylidene chloride layers 12 and 22: 1 μm, oxygen permeability: 9.7 cc/(m²·day·atm), water vapor permeability: 4.4 g/(m²·day)) having polyvinylidene chloride layers 12 and 22.

Example 5

Production of Multilayer Film for Disposable Body Warmer Outer Package Illustrated in FIG. 1

A multilayer film for a disposable body warmer outer bag, including unoriented polypropylene film 30/adhesive layer 40/biaxially oriented polyamide film 11/polyvinylidene chloride layer 12/adhesive layer 40/printing ink layer 50/polyvinylidene chloride layer 22/biaxially oriented polyamide film 21, when viewed from the lower layer, was produced in the same manner as in Example 1 except that biaxially oriented polyamide films 11 and 21 (thicknesses of biaxially oriented polyamide films 11 and 21: 25 μm, thicknesses of polyvinylidene chloride layers 12 and 22: 1 μm, oxygen permeability: 6.7 cc/(m²·day·atm), water vapor permeability: 9.7 g/(m²·day)) having polyvinylidene chloride layers 12 and 22 were used as the first and second barrier layers 10 and 20, instead of the biaxially oriented polypropylene films 11 and 21 (thicknesses of biaxially oriented polypropylene films 11 and 21: 30 μm, thicknesses of polyvinylidene chloride layers 12 and 22: 1 μm, oxygen permeability: 9.7 cc/(m²·day·atm), water vapor permeability: 4.4 g/(m²·day)) having polyvinylidene chloride layers 12 and 22.

Example 6

Production of Multilayer Film for Disposable Body Warmer Outer Package Illustrated in FIG. 1

A multilayer film for a disposable body warmer outer bag, including unoriented polypropylene film 30/adhesive layer 40/biaxially oriented polyethylene terephthalate film 11/polyvinylidene chloride layer 12/adhesive layer 40/printing ink layer 50/polyvinylidene chloride layer 22/biaxially oriented polyamide film 21, when viewed from the lower layer, was produced in the same manner as in Example 1 except that a biaxially oriented polyamide film 21 (thickness of biaxially oriented polyamide film 21: 25 μm, thickness of polyvinylidene chloride layer 22: 1 μm, oxygen permeability: 6.7 cc/(m²·day·atm), water vapor permeability: 9.7 g/(m²·day)) having a polyvinylidene chloride layer 22 was used as the second barrier layer 20, instead of the biaxially oriented polypropylene film 21 (thickness of biaxially oriented polypropylene film 21: 30 μm, thickness of polyvinylidene chloride layer 22: 1 μm, oxygen permeability: 9.7 cc/(m²·day·atm), water vapor permeability: 4.4 g/(m²·day)) having a polyvinylidene chloride layer 22, and a biaxially oriented polyethylene terephthalate film 11 (thickness of biaxially oriented polyethylene terephthalate film 11: 12 μm, thickness of polyvinylidene chloride layer 12: 1 μm, oxygen permeability: 8.1 cc/(m²·day·atm), water vapor permeability: 10 g/(m²·day)) having a polyvinylidene chloride layer 12 was used as the first barrier layer 10, instead of the biaxially oriented polypropylene film 11 (thickness of biaxially oriented polypropylene film 11: 30 μm, thickness of polyvinylidene chloride layer 12: 1 μm, oxygen permeability: 9.7 cc/(m²·day·atm), water vapor permeability: 4.4 g/(m²·day))) having a polyvinylidene chloride layer 12.

Example 7

Production of Multilayer Film for Disposable Body Warmer Outer Package Illustrated in FIG. 3

A multilayer film for a disposable body warmer outer package, including first and second barrier layers 10 and 20 consisting of heat-resistant resin substrates 11 and 21 (biaxially oriented polypropylene film 11, biaxially oriented polyethylene terephthalate film 21) and polyvinylidene chloride layers 12 and 22 obtained by coating at least one surface of each of the heat-resistant resin substrates 11 and 21 with polyvinylidene chloride, as illustrated in FIG. 3, was produced as follows.

An ether-based adhesive was applied onto a surface of a biaxially oriented polypropylene film 11 (thickness of biaxially oriented polypropylene film 11: 30 μm, thickness of polyvinylidene chloride layer 12: 1 μm, oxygen permeability: 9.7 cc/(m²·day·atm), water vapor permeability: 4.4 g/(m²·day)) having a polyvinylidene chloride layer 12, serving as the first barrier layer 10, the surface facing the polyvinylidene chloride layer 12, and dried, thereby forming an adhesive layer 40. A biaxially oriented polyethylene terephthalate film 21 (thickness of biaxially oriented polyethylene terephthalate film 21: 12 μm, thickness of polyvinylidene chloride layer 22: 1 μm, oxygen permeability: 8.1 cc/(m²·day·atm), water vapor permeability: 10 g/(m²·day)) having a polyvinylidene chloride layer 22, serving as the second barrier layer 20, was placed on the adhesive layer 40 so that the biaxially oriented polyethylene terephthalate film 21 and the adhesive layer 40 were in contact with each other, and subjected to lamination and integration. In addition, an ether-based adhesive was applied on a surface of the first barrier layer 10, the surface corresponding to the surface of the biaxially oriented polypropylene film 11, and dried, thereby forming an adhesive layer 40. An unoriented polypropylene film 30 (thickness: 20 μm, oxygen permeability: 1500 cc/(m²·day·atm), water vapor permeability: 8 g/(m²·day)) was placed on the adhesive layer 40, and subjected to lamination and integration. Furthermore, an ether-based adhesive was applied onto the polyvinylidene chloride layer 22 of the second barrier layer 20, and dried, thereby forming an adhesive layer 40. On the other hand, a character, a graphic, a sign, a picture and the like were printed on a biaxially oriented polypropylene film (thickness: 20 μm, oxygen permeability: 1500 cc/(m²·day·atm), water vapor permeability: 8 g/(m²·day)), serving as an additional resin layer 60, by use of a usual gravure ink composition with a gravure printing system, thereby forming a printing ink layer 50. The adhesive layer 40 adjacent to the polyvinylidene chloride layer 22 of the second barrier layer 20 was then laminated on and integrated to the printing ink layer 50 formed above, thereby producing a multilayer film for a disposable body warmer outer bag, including unoriented polypropylene film 30/adhesive layer 40/biaxially oriented polypropylene film 11/polyvinylidene chloride layer 12/adhesive layer 40/biaxially oriented polyethylene terephthalate film 21/polyvinylidene chloride layer 22/adhesive layer 40/printing ink layer 50/biaxially oriented polypropylene film 60, when viewed from the lower layer.

Examples 8 to 13

Production of Multilayer Film for Disposable Body Warmer Outer Package Illustrated in FIG. 3

Each multilayer film for a disposable body warmer outer bag was produced in the same manner as in Example 7 except that each film shown in Table 1 was used as the second barrier layer 20, instead of the biaxially oriented polyethylene terephthalate film 21 (thickness of biaxially oriented polyethylene terephthalate film 21: 12 μm, thickness of polyvinylidene chloride layer 22: 1 μm, oxygen permeability: 8.1 cc/(m²·day·atm), water vapor permeability: 10 g/(m²·day) having a polyvinylidene chloride layer 22, and each film shown in Table 1 was used as the additional resin layer 60, instead of the biaxially oriented polypropylene film (thickness: 20 μm, oxygen permeability: 1500 cc/(m²·day·atm), water vapor permeability: 8 g/(m²·day)).

TABLE 1

| | Second barrier layer | Additional resin layer |
|---|---|---|
| Example 8 | KOPP#20 | PET#12 |
| Example 9 | KONY#15 | PET#12 |
| Example 10 | KPET#12 | PET#12 |
| Example 11 | KOPP#20 | ONY#15 |
| Example 12 | KONY#15 | ONY#15 |
| Example 13 | KPET#12 | ONY#15 |

KPET#12: biaxially oriented polyethylene terephthalate film (thickness of biaxially oriented polyethylene terephthalate film: 12 μm, thickness of polyvinylidene chloride layer: 1 μm, oxygen permeability: 8.1 cc %(m²·day·atm), water vapor permeability: 10 g/(m²·day)) having polyvinylidene chloride layer KOPP#20: biaxially oriented polypropylene film (thickness of biaxially oriented polypropylene film: 20 μm, thickness of polyvinylidene chloride layer: 1 μm, oxygen permeability: 8.1 cc/(m²·day·atm), water vapor permeability: 5 g/(m²·day)) having polyvinylidene chloride layer KONY#15: biaxially oriented polyamide film (thickness of biaxially oriented polyamide film: 15 μm, thickness of polyvinylidene chloride layer: 1 μm, oxygen permeability: 8.1 cc/(m²·day·atm), water vapor permeability: 10 g/(m²·day)) having polyvinylidene chloride layer PET#12: biaxially oriented polyethylene terephthalate film (thickness: 12 μm, oxygen permeability: 80 cc/(m²·day·atm), water vapor permeability: 50 g/(m²·day))

ONY#15: biaxially oriented polyamide film (thickness: 15 μm, oxygen permeability: 30 cc/(m²·day·atm), water vapor permeability: 250 g/(m²·day))

Comparative Example 1

A biaxially oriented polypropylene film (thickness of biaxially oriented polypropylene film: 30 μm, thickness of polyvinylidene chloride layer: 1 μm, oxygen permeability: 9.7 cc/(m²·day·atm), water vapor permeability: 4.4 g/(m²·day)) having a polyvinylidene chloride layer was adopted, and a printing ink layer and an adhesive layer were formed on the polyvinylidene chloride layer in the same manner as in Example 1. A straight-chain low density polyethylene film (thickness: 30 μm, oxygen permeability: 5000 cc/(m²·day·atm), water vapor permeability: 16.6 g/(m²·day)) was placed on the adhesive layer, thereafter an adhesive layer was provided on the straight-chain low density polyethylene film in the same manner as in the above, and an ethylene-vinyl acetate copolymer film (thickness: 30 μm, oxygen permeability: 10000 cc/(m²·day·atm), water vapor permeability: 75 g/(m²·day)) was further placed thereon and subjected to lamination and integration, thereby producing a multilayer film for a disposable body warmer outer bag, including ethylene-vinyl acetate copolymer film/adhesive layer/straight-chain low density polyethylene film/adhesive layer/printing ink layer/polyvinylidene chloride layer/biaxially oriented polypropylene film, when viewed from the lower layer.

Comparative Example 2

A multilayer film for a disposable body warmer outer bag, including ethylene-vinyl acetate copolymer film/adhesive layer/straight-chain low density polyethylene film/adhesive layer/printing ink layer/polyvinylidene chloride layer/polyvinylidene chloride layer/biaxially oriented polypropylene film, when viewed from the lower layer, was produced in the same manner as in Comparative Example 1 except that a biaxially oriented polypropylene film (thickness of biaxially oriented polypropylene film: 30 μm, total thickness of two polyvinylidene chloride layers: 2 μm, oxygen permeability: 5.5 cc/($m^2$·day·atm), water vapor permeability: 4.4 g/($m^2$·day)) having two polyvinylidene chloride layers on one surface thereof was used instead of the biaxially oriented polypropylene film (thickness of biaxially oriented polypropylene film: 30 μm, thickness of polyvinylidene chloride layer: 1 μm, oxygen permeability: 9.7 cc/($m^2$·day·atm), water vapor permeability: 4.4 g/($m^2$·day)) having a polyvinylidene chloride layer. Herein, the two polyvinylidene chloride layers were produced by coating the biaxially oriented polypropylene film serving as a substrate with polyvinylidene chloride serving as a first layer, thereafter coating the resultant with polyvinylidene chloride serving as a second layer, and drying the resultant.

Comparative Example 3

A multilayer film for a disposable body warmer outer bag, including ethylene-vinyl acetate copolymer film/adhesive layer/straight-chain low density polyethylene film/adhesive layer/printing ink layer/thick polyvinylidene chloride layer/biaxially oriented polypropylene film, when viewed from the lower layer, was produced in the same manner as in Comparative Example 1 except that a biaxially oriented polypropylene film (thickness of biaxially oriented polypropylene film: 30 μm, thickness of polyvinylidene chloride layer: 2 μm, oxygen permeability: 5.5 cc/($m^2$·day·atm), water vapor permeability: 4.5 g/($m^2$·day)) having a thick polyvinylidene chloride layer was used instead of the biaxially oriented polypropylene film (thickness of biaxially oriented polypropylene film: 30 μm, thickness of polyvinylidene chloride layer: 1 μm, oxygen permeability: 9.7 cc/($m^2$·day·atm), water vapor permeability: 4.4 g/($m^2$·day)) having a polyvinylidene chloride layer.

Comparative Example 4

A printing ink layer and an adhesive layer were formed on one surface of a biaxially oriented polypropylene film (thickness: 20 μm, oxygen permeability: 1500 cc/($m^2$·day·atm), water vapor permeability: 8 g/($m^2$·day)) in the same manner as in Example 1. A biaxially oriented polyethylene terephthalate film (thickness: 12 μm, thickness of vapor-deposited layer: about 600 angstroms or less, oxygen permeability: 1.5 cc/($m^2$·day·atm), water vapor permeability 1.7 g/($m^2$·day)) having an aluminum vapor-deposited layer was placed on the adhesive layer so that the adhesive layer and the aluminum vapor-deposited layer were in contact with each other, and subjected to lamination and integration. Furthermore, an adhesive layer was formed on a surface of a biaxially oriented polyethylene terephthalate film having an aluminum vapor-deposited layer, the surface being opposite to the aluminum vapor-deposited layer, and thereafter a straight-chain low density polyethylene film (thickness: 30 oxygen permeability: 5000 cc/($m^2$·day·atm), water vapor permeability: 16.6 g/($m^2$·day)) was placed thereon, and subjected to lamination and integration, thereby producing a multilayer film for a disposable body wanner outer bag, including straight-chain low density polyethylene film/adhesive layer/biaxially oriented polyethylene terephthalate film/aluminum vapor-deposited layer/adhesive layer/printing ink layer/biaxially oriented polypropylene film, when viewed from the lower layer.

Reference Example

A character, a graphic, a sign, a picture and the like were printed on a surface of a biaxially oriented polypropylene film (thickness of biaxially oriented polypropylene film: 20 μm, thickness of polyvinylidene chloride layer: 1 oxygen permeability: 8.1 cc/($m^2$·day·atm), water vapor permeability: 5 g/($m^2$·day)) having a polyvinylidene chloride layer, the surface facing the polyvinylidene chloride layer, by use of a usual gravure ink composition with a gravure printing system, thereby forming a printing ink layer. Next, an ether-based adhesive was applied onto the printing ink layer formed above, and dried, thereby forming an adhesive layer. An unoriented polypropylene film (thickness: 25 μm, thickness of vapor-deposited layer: about 600 angstroms or less, oxygen permeability: 10 cc/($m^2$·day·atm), water vapor permeability: 0.5 g/($m^2$·day)) having an aluminum vapor-deposited layer was placed on the adhesive layer and subjected to lamination and integration so that the aluminum vapor-deposited layer and the adhesive layer were in contact with each other, thereby producing a multilayer film for a disposable body warmer outer bag, including unoriented polypropylene film/aluminum vapor-deposited layer/adhesive layer/printing ink layer/polyvinylidene chloride layer/biaxially oriented polypropylene film, when viewed from the lower layer.

(Evaluation)

The multilayer film for a disposable body warmer outer bag, produced in each of Examples 1 to 6, Comparative Examples 1 to 4 and Reference Example, was used to evaluate (1) oxygen permeability, (2) water vapor permeability, (3) appearance after acceleration test, (4) exothermic performance (duration) after acceleration test, (5) seal strength, (6) impact resistance, and (7) weather resistance as follows.

(1) Measurement of Oxygen Permeability

The following measurement machine was used under the following measurement conditions to measure the oxygen permeability (cc/($m^2$·day·atm)) under the following temperature and humidity conditions.

Temperature: 20° C.; humidity: 90% RH

Measurement machine: OX-TRAN 2/20 manufactured by Mocon Inc.; measurement method: continuous measurement 20 times every 30 minutes (2) Measurement of Water Vapor Permeability The following measurement machine was used under the following measurement conditions to measure the water vapor permeability (g/($m^2$·day)) under the following temperature and humidity conditions.

Temperature: 40° C.; humidity: 90% RH

Measurement machine: OX-TRAN 2/20 manufactured by Mocon Inc.; measurement method: continuous measurement 20 times every 30 minutes (3) Evaluation of Appearance After Acceleration Test Two of the multilayer films for disposable body warmer outer bag in each of Examples 1 to 6, Comparative Examples 1 to 4, and Reference Example were prepared, the thermal fusible substrates as sealant layers (Examples 1 to 6 and Reference Example: unoriented polypropylene film; Comparative Examples 1 to 3: ethylene-vinyl acetate copolymer film; Comparative Example 4: straight-chain low density polyethylene film) were allowed to face and were superposed, and thereafter the outer peripheries thereof were subjected to three-side heat-sealing to form a sealing portion and also produce a three-side heat-sealed disposable body warmer outer bag having an opening portion on the upper portion thereof.

An exothermic composition including 22 g of iron powder, 6 g of activated carbon, 6 g of a water-retaining agent and 10 g of water was prepared, and the exothermic composition was then charged and packaged in an inner bag to produce a stick type disposable body warmer including an individual package. One surface of the inner bag is formed from a porous sheet of a perforated polyethylene film as an air-permeable packaging material and the other surface thereof is formed from a polyethylene film as an air-impermeable packaging material.

Next, the disposable body warmer including an individual package, produced above, was charged through the opening portion of the disposable body warmer outer bag produced above, and thereafter the opening portion was heat-sealed to form an upper sealing portion, thereby producing a disposable body warmer product.

Five of the disposable body warmer products thus obtained were placed on a stage, and the height (mm) (hereinafter, referred to as "height H1 (mm)".) of the five disposable body warmer products stacked was measured. Next, the five disposable body warmer products stacked were stored at a temperature of 50° C. for 3 months, and the height (mm) of the five disposable body warmer products stacked was measured every 1 week for a period of 3 months. The height after a lapse of 3 months was defined as "height H2 (mm)". If any outer bag of the disposable body warmer products was swollen and broken during such a storage period, however, the maximum height before such breakage was defined as "height H2 (mm)". The value "H2 −H1 (mm)" was then calculated, and rated as the appearance after an acceleration test, according to the following criteria of Table 2.

TABLE 2

−2 < H2-H1 (mm) < 2: No change
−5 < H2-H1 (mm) ≤ −2: Slightly depressurizing tendency
H2-H1 (mm) ≤ −5: Depressurizing tendency
2 ≤ H2-H1 (mm) < 5: Slightly swelling tendency
5 ≤ H2-H1 (mm): Swelling tendency (4) Evaluation of Exothermic Performance (Duration) After Acceleration Test A disposable body warmer product was produced in the same manner as in "(3) Evaluation of appearance after acceleration test" above.

The disposable body warmer outer bags of ten of the disposable body warmer products thus obtained were opened to take out respective disposable body warmers, and the exothermic performance of each of the disposable body warmers was tested based on JIS S4100. The duration average was defined as the "exothermic performance (duration). initial" (hereinafter, referred to as "durationT1".).

On the other hand, the ten disposable body warmer products obtained above were stored at a temperature of 50° C. for three months, thereafter respective disposable body warmer outer bags were opened to take out respective disposable body warmers, and the exothermic performance of each of the disposable body warmers was tested based on JIS S4100. The duration average was defined as "exothermic performance (duration)·after acceleration test" (hereinafter, referred to as "durationT2".).

The value T2/T1×100 (%) was then calculated, and rated as the exothermic performance (duration) in the evaluation after an acceleration test, according to the following criteria of Table 3.

TABLE 3

95 < T2/T1 × 100 (%) ≤ 100: S (Excellent)
90 < T2/T1 × 100 (%) ≤ 95: A (Favorable)
80 < T2/T1 × 100 (%) ≤ 90: B (Usable)
T2/T1 × 100 (%) ≤ 80: C (Not suitable as product)
Any heat-sealing portion was broken due to swelling, and heat generation was terminated before product opening.:- (Not suitable as product)

(5) Seal Strength

Two of the multilayer films for a disposable body warmer outer bag, produced in each of Examples 1 to 6, Comparative Examples 1 to 4, and Reference Example, were prepared, the thermal fusible substrates as sealant layers (Examples 1 to 6 and Reference Example: unoriented polypropylene film, Comparative Examples 1 to 3: ethylene-vinyl acetate copolymer film, Comparative Example 4: straight-chain low density polyethylene film) were allowed to face and were superposed, and thereafter a heat-sealing portion having a sealing width of 10 mm was formed over the entire length of one end side of the multilayer films for a disposable body wanner outer bag superposed, in conditions of a temperature of 160° C., a pressure of 0.25 MPa and a time of 0.5 seconds. A laminated body of two of the multilayer films for a disposable body warmer outer bag, having such a heat-sealing portion, was cut out to provide three strip-shaped samples of 15 mm in width×50 mm in length (including a heat-sealing portion of 15 mm in width× 10 mm in length), and the peeling strength (N/15 mm) of each of the samples was measured with a tensile tester (manufactured by TCE Co., Ltd., product name: AUTO-COM) at a tension rate of 300 mm/min and a distance between grips of 10 mm, and the average thereof was calculated.

While the seal strength can fall within the numerical range of 13.0 N/15 mm or more to thereby cause no large problem in use as an outer bag for a disposable body warmer, the seal strength can fall within the numerical range of 15.0 N/15 mm or more to thereby allow an outer bag to be hardly opened or ruptured even when the outer bag is subjected to external high impact.

(6) Evaluation of Impact Resistance (6-1) Transportation Test

A disposable body warmer product was produced in the same manner as in "(3) Evaluation of appearance after acceleration test" above.

Sixty four of the disposable body warmer products thus obtained were prepared with respect to each sample in Examples 1 to 6, Comparative Examples 1 to 4 and Reference Example, the sixty four of the disposable body warmer products were packed in one cardboard box (15 cm in height×36.5 cm in width ×25.3 cm in depth) with respect to each sample, and the cardboard box was transported from Osaka in Japan to Shanghai in China by an international cargo flight and received in Shanghai in China, and thereafter sent back to Osaka in Japan by a similar transport flight. The sixty four of the disposable body wanner products were taken out from the cardboard box thus transported, and all of them were visually confirmed about whether the outer bags were opened and ruptured or not. In addition, an ageless examination was performed as follows: the outer bags of the sixty four of the disposable body warmer products visually confirmed were holed at any position other than the heat-sealing portions thereof, a penetrant (components: fatty acid ester, high-boiling point hydrocarbon and red paint) was sprayed into each of the outer bags, and whether the penetrant was leaked through each of the heat-sealing portions or not was confirmed. The results were rated with respect to the transportation test according to the following criteria in Table 4 below.

TABLE 4

Neither opening nor rupture was visually observed in outer bags of all of 64 specimens, and no penetrant leakage from each heat-sealing portion of all of 64 specimens was confirmed in an ageless examination.
: A (Favorable)
Opening or rupture was visually observed in a part or all of outer bags of 64 specimens, and/or penetrant leakage from any heat-sealing portion of a part or all of outer bags of 64 specimens was confirmed in an ageless examination.
: B (while there was no large problem in use as an outer bag for a disposable body warmer, impact resistance was slightly poor.)

(6-2) Drop Test

A disposable body warmer product was produced in the same manner as in "(3) Evaluation of appearance after acceleration test" above.

Sixty four of the disposable body wanner products thus obtained were prepared with respect to each sample in Examples 1 to 6, Comparative Examples 1 to 4 and Reference Example, the sixty four of the disposable body warmer products were packed in one cardboard box (15 cm in height×36.5 cm in width×25.3 cm in depth) with respect to each sample, and the cardboard box was freely dropped from a height of 1 m onto an iron plate horizontally located on the ground ten times in total including once in each of one corner, three edges and six sides. The sixty four of the disposable body warmer products were taken out from the cardboard box thus dropped, and all of them were visually confirmed about whether the outer bags were opened and ruptured or not. In addition, an ageless examination was performed to confirm whether the penetrant was leaked through each of the heat-sealing portions in the same manner as in "(6-1) Transportation test" above. The results were rated with respect to the drop test according to the criteria of "(6-1) Transportation test" above in Table 4.

(7) Evaluation of Weather Resistance

A disposable body warmer product was produced in the same manner as in "(3) Evaluation of appearance after acceleration test" above.

The disposable body warmer product thus obtained was irradiated with light by use of a xenon weather meter (6.5 kW xenon arc lamp type accelerated weather resistance tester manufactured by Toyo Seiki Seisaku-sho, Ltd., Atlas Ci4000) in conditions of an irradiance of 0.35 W/m$^2$, a wavelength of 300 to 800 nm, a black panel temperature of 42° C., a humidity of 52% RH and 20 hours, to perform an accelerated weather resistance test.

The appearance of the disposable body warmer product irradiated with light was then observed, and the results were rated with respect to the weather resistance according to the following criteria in Table 5 below.

TABLE 5

There was not observed any change in appearance such as discoloration at all.
: S (Excellent)
There was slightly observed any change in appearance such as discoloration.
: A (Favorable)
There was remarkably observed any change in appearance such as discoloration.
: B (while there was no large problem in use as an outer bag for a disposable body warmer, weather resistance was slightly poor.)

TABLE 6

|  | Oxygen permeability (cc/(m$^2$ · day · atm)) | Water vapor permeability (g/(m$^2$ · day)) | H2-H1 (mm) | Evaluation of appearance | Exothermic performance (duration) |
|---|---|---|---|---|---|
| Example 1 | 3.2 | 1.7 | 0 | No change | S |
| Example 2 | 3.0 | 2.0 | 1 | No change | S |
| Example 3 | 2.6 | 2.2 | 0 | No change | S |
| Example 4 | 2.8 | 2.8 | 0 | No change | A |
| Example 5 | 2.2 | 3.3 | −3 | Slightly depressurizing tendency | B |
| Example 6 | 2.5 | 2.6 | −1 | No change | A |
| Comparative Example 1 | 5.9 | 4.9 | −8 | Depressurizing tendency | C |
| Comparative Example 2 | 5.5 | 4.4 | −7 | Depressurizing tendency | C |
| Comparative Example 3 | 5.5 | 4.5 | −7 | Depressurizing tendency | C |
| Comparative Example 4 | 0.9 | 0.7 | 13 | Swelling tendency | — |
| Reference Example | 3.7 | 0.5 | 0 | No change | S |

TABLE 7

|  |  | Evaluation of impact resistance |  |  |
|---|---|---|---|---|
|  | Seal strength (N/15 mm) | Transportation test | Drop test | Evaluation of weather resistance |
| Example 1 | 56.2 | A | A | A |
| Example 2 | 58.4 | A | A | A |
| Example 3 | 57.3 | A | A | A |
| Example 4 | 60.5 | A | A | A |
| Example 5 | 54.7 | A | A | A |
| Example 6 | 55.2 | A | A | A |
| Comparative Example 1 | 23.9 | A | A | A |
| Comparative Example 2 | 26.2 | A | A | A |
| Comparative Example 3 | 25.1 | A | A | A |
| Comparative Example 4 | 46.7 | A | A | S |
| Reference Example | 13.9 | B | B | B |

When the rating of the appearance in Table 6 above is "No change", a disposable body warmer product is not changed in appearance even after storage for a long period and thus can be sold into a market as a product. On the other hand, when the rating of the appearance in Table 6 above is "Slightly depressurizing tendency", "Depressurizing tendency", "Slightly swelling tendency" or "Swelling tendency", a disposable body warmer product is not preferable because of being changed in appearance after storage for a long period.

As clear from the results in Table 6 above, in Examples 1 to 4 and 6, no change in appearance of a package product was observed before and after an acceleration test and no degradation in exothermic function as a product was caused even after storage for a long period. In addition, in Examples 1 to 6, the disposable body warmer outer bag was low in water vapor permeability to allow water vapor to hardly penetrate, thereby allowing moisture to hardly penetrate from the exterior into the interior of the outer bag, and allowing moisture included as a component of the disposable body warmer to hardly escape to the outside, and therefore sufficiently served as a disposable body warmer even after storage for a long period. Furthermore, as clear from the results in Table 7 above, in Examples 1 to 6, seal strength and impact resistance were excellent and therefore each of the outer bags was not opened and ruptured even when subjected to external high impact. Additionally, in Examples 1 to 6, weather resistance was excellent and therefore each of the outer bags did not cause any change in appearance such as discoloration even when exposed to ultraviolet light such as sunlight.

On the other hand, in Comparative Examples 1 to 4, any change in appearance of a package product was observed before and after an acceleration test and each disposable body wanner product was not preferable in terms of appearance after storage for a long period. In addition, in Comparative Examples 1 to 3, each outer bag was slightly high in water vapor permeability to cause water vapor to easily penetrate, thereby causing moisture to easily penetrate from the exterior into the interior of the outer bag, and also causing moisture included as an exothermic composition component of each disposable body warmer to easily escape to the outside, and therefore did not sufficiently generate heat as a disposable body warmer after storage for a long period. Furthermore, in Comparative Example 4, swelling tendency was remarkably observed, and such swelling caused each heat-sealing portion to be broken, and each body warmer was brought into contact with outside air to terminate heat generation before each product was opened.

In Reference Example, no change in appearance of a package product was observed before and after an acceleration test and no degradation in exothermic function as a product was caused even after storage for a long period. In addition, in Reference Example, the disposable body warmer outer bag was low in water vapor permeability to allow water vapor to hardly penetrate, thereby allowing moisture to hardly penetrate from the exterior into the interior of the outer bag, and allowing moisture included as a component of the disposable body warmer to hardly escape to the outside, and therefore sufficiently served as a disposable body warmer even after storage for a long period. While the disposable body warmer outer bag thus had no large problem as a product, it was lower in seal strength, impact resistance and weather resistance than Examples 1 to 6, as clear from the results in Table 7.

In addition, the exothermic composition was charged and packaged in an inner bag to produce a non-stick type disposable body warmer including an individual package. One surface of the inner bag is formed from a porous sheet of a perforated polyethylene film as air-permeable packaging material and the other surface thereof is formed from a polyethylene film as an air-impermeable packaging material. Such a disposable body warmer was tested in the same manner as in Examples 1 to 6, and favorable results were similarly obtained as in Examples 1 to 6.

REFERENCE SIGNS LIST

10 first barrier layer
11 heat-resistant resin substrate
12 polyvinylidene chloride layer
20 second barrier layer
21 heat-resistant resin substrate
22 polyvinylidene chloride layer
30 sealant layer
40 adhesive layer
50 printing ink layer
60 additional resin layer

The invention claimed is:

1. A multilayer film for a disposable body warmer outer bag, comprising:
   two or more barrier layers each consisting of a substrate and a polyvinylidene chloride layer obtained by coating at least one surface of the substrate with polyvinylidene chloride; and
   an adhesive layer between the two or more barrier layers, wherein
   the multilayer film does not comprise any vapor-deposited layer obtained by vapor-depositing a metal or metal oxide, and
   the multilayer film has 1.5 to 4.5 cc/(m$^2$·day·atm) of an oxygen permeability measured at 20 °C. and 90% RH, and 0.05 to 3.5 g/(m$^2$·day) of a water vapor permeability measured at 40 °C. and 90% RH.

2. The multilayer film for a disposable body warmer outer bag according to claim 1, wherein each of the substrates of said two or more barrier layers is selected from biaxially oriented polypropylene, biaxially oriented polyethylene terephthalate and a biaxially oriented polyamide resin.

3. The multilayer film for a disposable body warmer outer bag according to claim 1, further comprising a sealant layer comprising a thermal fusible resin substrate.

4. The multilayer film for a disposable body warmer outer bag according to claim 1, further comprising an additional resin layer.

5. The multilayer film for a disposable body warmer outer bag according to claim 1, wherein each of the polyvinylidene chloride layers of the two or more barrier layers faces the adhesive layer.

6. The multilayer film for a disposable body warmer outer bag according to claim 1, further comprising:
   a sealant layer comprising a thermal fusible resin substrate and an additional resin layer, wherein
   each of the substrates of said two or more barrier layers is a heat-resistant resin substrate and the thickness of the heat-resistant resin substrate is 3 to 500 μm,
   each of the polyvinylidene chloride layers of two or more barrier layers has a thickness of 0.5 to 30 μm, and
   a thickness of the sealant layer is 5 to 300 μm and a thickness of the additional resin layer is 3 to 500 μm.

7. A disposable body warmer obtained by packaging airtightly an inner bag accommodating an exothermic composition, in an outer bag formed by thermal fusion of the multilayer film for a disposable body warmer outer bag according to claim 1.

\* \* \* \* \*